United States Patent
Saks et al.

(10) Patent No.: US 6,618,861 B2
(45) Date of Patent: Sep. 16, 2003

(54) MEDICAL GLOVES WITH WATCH VIEWING CAPABILITIES

(75) Inventors: Nathan M. Saks, Reno, NV (US); Jian Jim Tao, Reno, NV (US)

(73) Assignee: Microflex Corporation, Reno, NV (US)

( * ) Notice: Subject to any disclaimer, the term of this patent is extended or adjusted under 35 U.S.C. 154(b) by 8 days.

(21) Appl. No.: 09/956,345

(22) Filed: Sep. 20, 2001

(65) Prior Publication Data

US 2002/0133864 A1 Sep. 26, 2002

Related U.S. Application Data

(60) Provisional application No. 60/258,310, filed on Dec. 28, 2000.

(51) Int. Cl.[7] .............................................. A41D 19/00
(52) U.S. Cl. ........................................ 2/161.7; 264/305
(58) Field of Search ............................. 2/161.7, 161.6, 2/162, 167, 169, 170, 59; 264/305

(56) References Cited

U.S. PATENT DOCUMENTS

| | | | |
|---|---|---|---|
| 1,924,617 A | 8/1933 | Miller | |
| 2,418,887 A | 4/1947 | Jones | |
| 2,670,473 A | 3/1954 | Stebic | |
| 4,387,838 A | * 6/1983 | Jackson | 224/170 |
| 4,757,557 A | * 7/1988 | Hirano | 2/125 |
| 5,332,135 A | * 7/1994 | Fletcher | 224/164 |
| 5,734,992 A | 4/1998 | Ross | |
| 5,924,135 A | * 7/1999 | Worth | 2/125 |

* cited by examiner

Primary Examiner—John J. Calvert
Assistant Examiner—Katherine Moran
(74) Attorney, Agent, or Firm—Evan Kent; Stewart Gitler

(57) ABSTRACT

A method of multiple dipping to make gloves with a clear wrist portion, which allows glove wearers to see through the transparent wrist portion and tell time with the gloves on, is disclosed. The method is applicable to all the common materials to make gloves, or coat gloves, via dipping: including natural rubber latex, nitrile rubber latex (carboxylated or non-carboxylated), polychloroprene latex, polyisoprene latex, polyurethane latex, polyvinyl chloride and their blends, or mixtures thereof. The invention provides procedures to make compounds, which are both transparent and opaque, as well as dipping sequences for the materials. Products, with the added feature of a transparent wrist portion, are provided without sacrificing performance and without increasing production cost.

9 Claims, 2 Drawing Sheets

MEDICAL GLOVES WITH WATCH VIEWING CAPABILITIES

This application claims benefit of Prov. No. 60/258,310 filed Dec. 28, 2000.

BACKGROUND OF THE INVENTION

Traditionally, medical examination and surgical gloves are made via a latex dipping method. Some common materials employed include: natural rubber latex (NRL), nitrile rubber (NBR), polychloroprene (CR), polyurethane (PU), polyvinyl chloride (PVC), polyethylene (PE), polyisoprene latex and their mixed blends. The production process involves the following steps: coagulant dipping, latex dipping, leaching, vulcanization, and mold stripping. The coagulant dipping step is a straight forward single dipping procedure. However, the latex dipping step could be a multiple dipping procedure. One could repeat dipping in the same compound to increase thickness or use different compounds for various functionalities.

Some prior patents exist which display gloves which are translucent in appearance.

Stebic (U.S. Pat. No. 2,670,473) discloses a transparent glove worn to reveal the texture and color of skin. The texture and color of the skin is the background for the product being handled. There is no contemplation of a medical glove with a clear wrist portion for displaying a timepiece.

Jones (U.S. Pat. No. 2,418,887) discloses a glove made from connected sections. One or more sections, such as a lower wrist covering section 8, may be omitted for displaying a bracelet or wristwatch. There is no contemplation of a medical glove with a clear wrist portion for displaying a timepiece.

Miller (U.S. Pat. No. 1,924,617) discloses a latex glove which is highly translucent. Objects placed against the glove are visible from the other side of the glove. There is no contemplation of a medical glove with a clear wrist portion for displaying a timepiece.

Ross (U.S. Pat. No. 5,734,992) discloses a two-piece glove having a glove portion and arm covering portion. The two portions may be made of similar or different materials. Materials useable for the arm portion include polyethylene, polyvinyl chloride, vinyl or nitrile. There is no contemplation of a medical glove with a clear wrist portion for displaying a timepiece.

SUMMARY OF THE INVENTION

This invention describes a multiple dipping process (coagulant dipping and latex dipping) to make gloves with a clear wrist portion, which allows glove wearers to tell time with the gloves on. This product provides tremendous convenience to wearers who need to monitor time constantly, Emergency Medical Staff, for example. The methodology disclosed is applicable to all the materials mentioned above. The formulations for clear, or opaque compounds are also included.

DETAILED DESCRIPTION OF INVENTION

Figure 1:
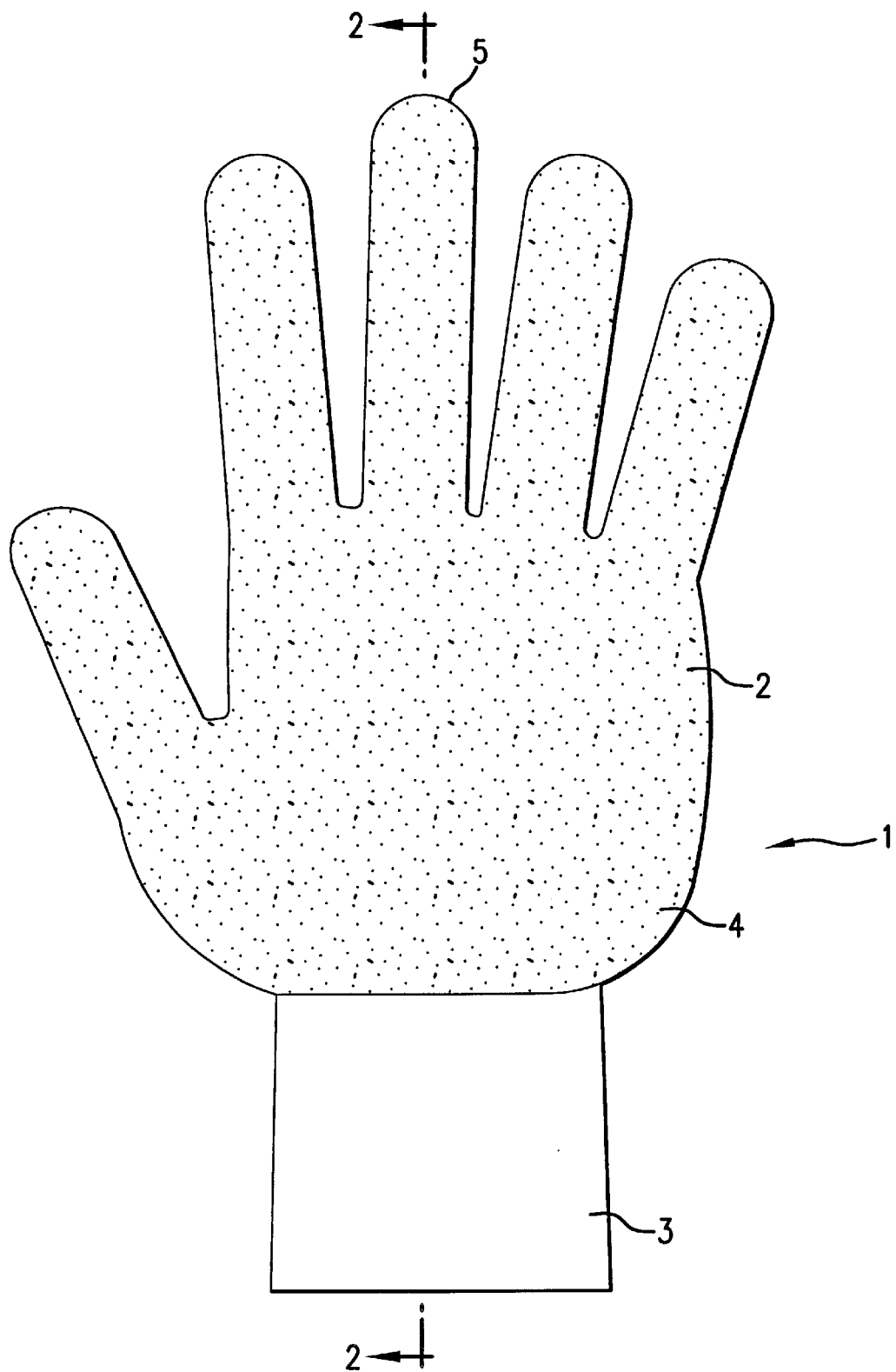
FIG. 1 depicts a glove embodied by the invention.
Figure 2:
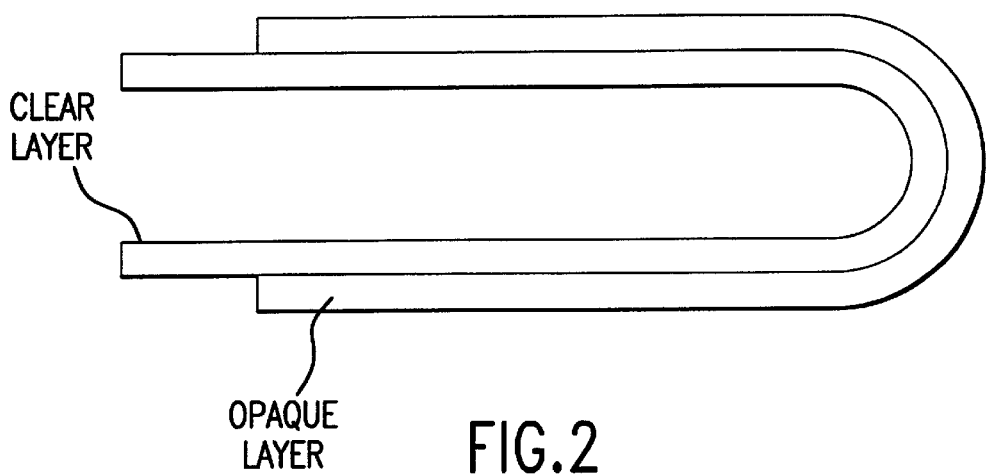
FIG. 2 is a cross-sectional view of the glove along line 2-2 of FIG. 1.
Figure 3:
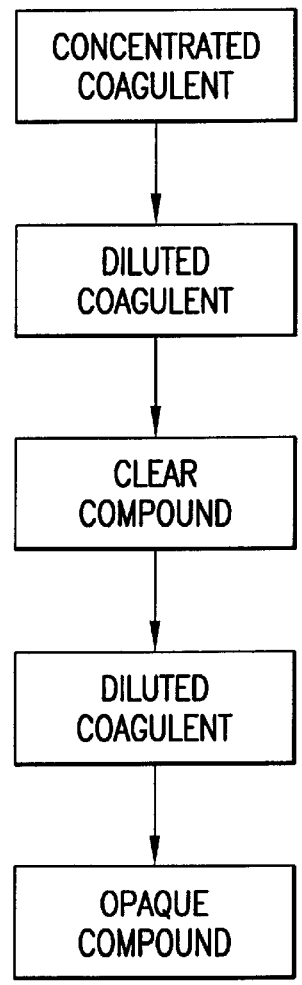
FIG. 3 is a flow chart of the method of making the glove of the invention.

Compounding:

In order to make a product with two distinct portions, one portion clear and the other opaque, two latex compounds are prepared separately. As we mentioned earlier, the method applies to all conventional materials for glove dipping. To illustrate the process, three compounding examples for nitrile latex, polyisoprene latex, and their binary blend are given together with mechanical properties of the resulting films. The coagulant is a calcium nitrate aqueous solution with additives, such as mold releasing agents, defoamers, surfactants, and the like.

The opaque compound utilized, is one commonly used in the glove manufacturing process. Titanium dioxide($TiO_2$) is utilized and it does not contribute to the overall mechanical properties of the finished product. Therefore, the lack of Titanium dioxide in the transparent portion of the glove does not affect the overall properties of the two distinct compounds during vulcanization.

The mechanical properties of the films made from the two compounds are identical, within experimental errors. This ensures that delamination between two layers will not occur, even under stress.

EXAMPLE 1

Nitrile Compounding

| Ingredient | PHR |
| --- | --- |
| Nitrile Latex | 100 |
| 2,2'-methylene-bis-(4-methyl-6-t-butylphenol) | 0.5 |
| Sulfur | 1.5 |
| Zinc 2-mercaptobenzothiazole | 0.5 |
| Zinc Dibutyldithiocarbarnate | 0.5 |
| Titanium Dioxide | 0.5 |
| KOH | 1.0 |

| Modulus at 300% (MPa) | Ultimate Elongation (%) | Ultimate Tensile Strength (MPa) |
| --- | --- | --- |
| 2.12 | 689 | 19.18 |

The typical mechanical properties are tabulated as follows (meeting ASTM requirements):

EXAMPLE 2

Polyisoprene Compounding

| Ingredient | PHR |
| --- | --- |
| Polyisoprene Latex | 100 |
| 2,2'-methylene-bis-(4-methyl-6-t-butylphenol) | 0.3 |
| 2,6-di-tert-butyl-4-methylphenol | 0.2 |
| Sulfur | 0.3 |
| Tetramethylthiuram Disulfide | 2.0 |
| Zinc Oxide | 0.5 |
| Zinc 2-mercaptobenzothiazole | 0.2 |
| Zinc Dibutyldithiocarbarnate | 0.2 |
| 1,3-diphenyl-2-thiourea | 0.2 |
| Zinc Diethyldithiocarbarnate | 0.2 |
| Titanium Dioxide | 0.5 |

The typical mechanical properties are tabulated as follows.

| Modulus at 300% (MPa) | Ultimate Elongation (%) | Ultimate Tensile Strength (MPa) |
| --- | --- | --- |
| 1.03 | 1028 | 13.22 |

EXAMPLE 3
Nitrile and Polyisoprene Blend

| Ingredient | PHR |
| --- | --- |
| Nitrile Latex | 80 |
| Polyisoprene Latex | 20 |
| 2,2'-methylene-bis-(4-methyl-6-t-butylphenol) | 0.5 |
| Tetramethylthiuram Disulfide | 2.0 |
| Zinc 2-mercaptobenzothiazole | 0.2 |
| Zinc Dibutyldithiocarbarnate | 0.2 |
| Titanium Dioxide | 0.5 |
| Potassium Hydroxide | 1.0 |

| Modulus at 300% (MPa) | Ultimate Elongation (%) | Ultimate Tensile Strength (MPa) |
| --- | --- | --- |
| 1.69 | 795 | 11.57 |

Dipping:
Procedure 1:
Procedure 1 is simpler and straightforward.

| | |
| --- | --- |
| Dipping tank 1: | Coagulant full depth |
| Dipping tank 2: | Clear compound full depth |
| Dipping tank 3: | Opaque compound partial depth from fingertips to palm |

Then, the drying, leaching, and vulcanization steps follow. The resulting product has a clear wrist portion to allow wearers to see through the glove and tell the time from the watch underneath the wrist portion of the glove.
Procedure 2:
Procedure 1 works very well in terms of product performance, i.e., watch viewing capability. However, the thickness is not as uniform as desired. The lower portion is thicker due to double dipping. To control the overall thickness, a more sophisticated dipping procedure has been developed.

| | |
| --- | --- |
| Dipping tank 1: | Concentrated coagulant with mold releasing agent, full depth |
| Dipping tank 2: | Diluted coagulant with mold releasing agent, partial depth |
| Dipping tank 3: | Clear compound full depth |
| Dipping tank 4: | Diluted dipping coagulant without mold releasing agent, partial depth(in the case of natural rubber latex, this step is omitted) |
| Dipping tank 5: | Opaque compound partial depth |

By adjusting the parameters like coagulant concentration, compound viscosity, dipping dwell duration, and the like, one can produce gloves with a desired thickness from wrist to finger tips and with a clear wrist portion and opaque lower portions. The drying, leaching, and vulcanization steps follow.

Mechanical characterization of such gloves has been conducted. Nothing unusual has been observed. No delamination occurs between layers. No weak spots or defects have been found at the conjunction line as evidenced by the testing results.

FIG. 1 depicts a glove 1 having a clear wrist portion 3 and an opaque section 2 running from the palm 4 to the fingertips 5.

The invention as described is limited only by the scope of the claims. Modifications and variations are not to be regarded as a departure from the principles herein and are only limited by the claims.

What is claimed is:

1. A glove having a clear wrist portion and an opaque portion running from fingertips to a palm of the glove wherein the glove is produced by the steps of:

(i) forming the glove by dipping a form mold in a dipping tank to form a first layer of a coagulant coating on the form mold;

(ii) forming a second clear coating layer over the first layer by dipping the form mold in a second dipping tank, the clear coating forming the innermost layer; and (iii) forming a third opaque coating layer over the second coating layer by dipping the form mold in a third dipping tank to a partial depth from fingertips to palm of the form mold.

2. A glove as claimed in claim 1, further comprising the step of dipping the form mold into a fourth dipping tank, between the first dipping tank and the second dipping tank, containing a diluted coagulant with mold releasing agent to a partial depth.

3. A glove as claimed in claim 2, further comprising the step of dipping the form mold into a fifth dipping tank between the second dipping tank and the third dipping tank, into a diluted dipping coagulant without a mold release agent to a partial depth.

4. A glove, comprising:
   a finger portion,
   a palm portion extending from said finger portion and forming a bottom of said glove,
   a back portion extending from said finger portion and forming a top of said glove,
   a wrist portion integral with, and extending from, said palm portion and said back portion, and
   wherein the entire said wrist portion allows more transmission of light than said palm and back portions.

5. The glove of claim 4, wherein said wrist portion is transparent and said back and palm portions are non-transparent.

6. The glove of claim 5, wherein said back and palm portions are opaque.

7. A glove, comprising:
   a finger portion,
   a palm portion extending from said finger portion and forming a bottom of said glove,
   a back portion extending from said finger portion and forming a top of said glove,
   a wrist portion integral with said palm portion and said back portion,
   a transparent layer extending the entire length of the glove from said finger portion to said wrist portion,
   a non-transparent layer extending only a partial length of the glove, said partial length being the finger portion and said palm portion, and
   the portion of the glove extending from said palm being transparent.

8. The glove of claim 7, wherein said non-transparent layer is opaque.

9. The glove of claim 7, wherein said transparent layer is the innermost layer of said glove.

* * * * *